United States Patent

Kast et al.

[11] 4,052,398
[45] Oct. 4, 1977

[54] DIAZARHODAMINE-LACTONES, THEIR MANUFACTURE AND THEIR USE AS DYE INTERMEDIATES FOR COPYING PROCESSES

[75] Inventors: Hellmut Kast, Bobenheim-Roxheim; Guenter Dunkelmann, Ludwigshafen, both of Germany

[73] Assignee: BASF Aktiengesellschaft, Ludwigshafen, Germany

[21] Appl. No.: 657,861

[22] Filed: Feb. 13, 1976

[30] Foreign Application Priority Data

Mar. 6, 1975 Germany .............................. 2509793

[51] Int. Cl.$^2$ .......................................... C07D 491/20
[52] U.S. Cl. ..................... 260/256.4 F; 260/256.4 N; 260/517; 260/256.5 R; 544/115; 260/243.3
[58] Field of Search ................................. 260/256.4 F

[56] References Cited

U.S. PATENT DOCUMENTS

| | | | |
|---|---|---|---|
| 3,896,128 | 7/1975 | Kast et al. ............... | 260/256.4 F |
| 3,931,182 | 1/1976 | Kast et al. ............... | 260/256.4 F |

OTHER PUBLICATIONS

Kast et al., Chem. Abs. 82, 100085 (1975).

Primary Examiner—Donald G. Daus
Assistant Examiner—Mark L. Berch
Attorney, Agent, or Firm—Keil, Thompson & Shurtleff

[57] ABSTRACT

New diazarhodamine-lactones of the formula (I)

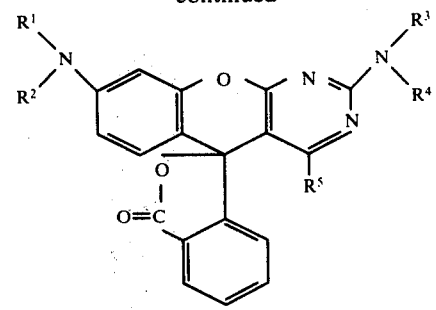

where $R^1$ is hydrogen or alkyl of 1 to 4 carbon atoms, $R^2$ is alkyl of 1 to 4 carbon atoms, unsubstituted phenyl or phenyl substituted by one or two alkyls of 1 to 3 carbon atoms, chlorine and/or bromine, $R^3$ and $R^4$ independently of one another are hydrogen, alkyl of 1 to 7 carbon atoms, cycloalkyl of 5 to 7 carbon atoms, phenylalkyl of 7 to 10 carbon atoms or alkoxyalkyl of a total of 3 to 8 carbon atoms, or the group

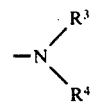

is a 5-membered, 6-membered or 7-membered saturated heterocyclic ring or a 6-membered saturated heterocyclic ring which additionally contains an —O—, —S— or —N—group, wherein $R^6$ is hydrogen, methyl or ethyl and $R^5$ is unsubstituted phenyl or phenyl substituted by alkyl of 1 to 3 carbon atoms, methoxy, chlorine or bromine.

The lactones (I) exhibit improved stability and therefore do not stain coated paper. On papers coated with acid receptive layers, copies which instantly exhibit their full depth of color are obtained.

6 Claims, No Drawings

DIAZARHODAMINE-LACTONES, THEIR MANUFACTURE AND THEIR USE AS DYE INTERMEDIATES FOR COPYING PROCESSES

The present invention relates to diazarhodamine-lactones of the formula I

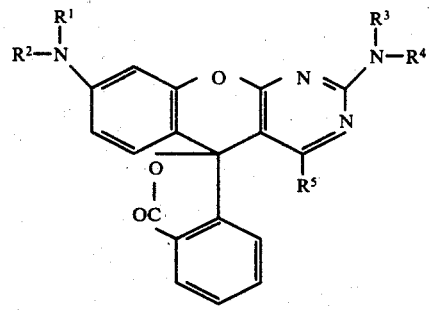

where $R^1$ is hydrogen or alkyl of 1 to 4 carbon atoms, $R^2$ is alkyl of 1 to 4 carbon atoms, unsubstituted phenyl, or phenyl in which 1 or 2 hydrogens are replaced by alkyl of 1 to 3 carbon atoms, chlorine or bromine, the substituents being identical or different, $R^3$ und $R^4$ independently of one another are hydrogen, alkyl of 1 to 7 carbon atoms, cycloalkyl of 5 to 7 carbon atoms, phenylalkyl of 7 to 10 carbon atoms or alkoxyalkyl of a total of 3 to 8 carbon atoms, or the group

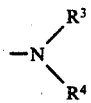

is a 5-membered, 6-membered or 7-membered saturated heterocyclic ring or a 6-membered saturated heterocyclic ring which additionally contains one of the groups —O—, —S— and

as a ring member, $R^6$ being hydrogen, methyl or ethyl, and $R^5$ is unsubstituted phenyl or phenyl which is substituted by alkyl of 1 to 3 carbon atoms, methoxy, ethoxy, chlorine or bromine.

The following are examples of the substituents $R^1$, $R^2$, $R^3$, $R^4$ and $R^5$:

$R^1$: hydrogen or preferably methyl, ethyl, propyl and butyl.

$R^2$: methyl, ethyl, propyl, butyl, phenyl, o-tolyl, p-tolyl, o-chlorophenyl, p-chlorophenyl, 2,4-dichlorophenyl, p-bromophenyl and chlorotolyl; $R^1$ is preferably hydrogen if $R^2$ is unsubstituted phenyl or phenyl substituted by methyl, chlorine and/or bromine.

$R^3$ and $R^4$: hydrogen or, independently of one another, methyl, ethyl, propyl, butyl, isobutyl, pentyl, 1,1-dimethylpropyl, cyclopentyl, cyclohexyl, benzyl, phenylethyl, β-methoxyethyl, β-ethoxyethyl, β-propoxyethyl, β-butoxyethyl, β-methoxypropyl, β-ethoxypropyl, β-butoxypropyl, γ-methoxypropyl, γ-ethoxypropyl and γ-butoxypropyl.

as the radical of a heterocyclic 5-membered, 6-membered or 7-membered ring: the radical of pyrrolidine, piperidine, morpholine, 3,5-dimethyl-morpholine, thiomorpholine, piperazine, N-methylpiperazine, N-ethylpiperazine or hexamethyleneimine.

$R^5$: phenyl, p-chlorophenyl, p-methoxyphenyl, p-ethoxyphenyl, p-tolyl, p-ethylphenyl and p-bromophenyl.

Dye intermediates which are industrially particularly important are the lactones of the formula I, where $R^1$ is methyl or ethyl and $R^2$ is methyl or ethyl, or $R^1$ is hydrogen and $R^2$ is o-tolyl, p-tolyl, o-chlorophenyl or p-chlorophenyl, $R^3$ and $R^4$ independently of one another are alkyl of 1 to 4 carbon atoms, eg. methyl, ethyl, propyl or butyl, cyclohexyl, benzyl, β-methoxyethyl or β-ethoxyethyl or $R^3$ and $R^4$ together with the nitrogen are a pyrrolidine, piperidine or N-methylpiperazine ring, and $R^5$ is phenyl or methoxyphenyl.

Amongst the above, particularly preferred lactones are those where $R^1 = R^2$, and each is methyl or ethyl, and $R^3$, $R^4$ and $R^5$ have the above meanings. Very particularly preferred diazarhodamine-lactones of the formula (I) are those where $R^1$ and $R^2$ are methyl or ethyl, $R^3$ and $R^4$ are butyl and $R^5$ is phenyl or methoxyphenyl.

The diazarhodamine-lactones of the formula I may be manufactured by condensing benzoylbenzoic acids of the formula

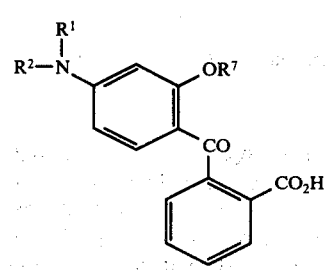

with pyrimidines of the formula

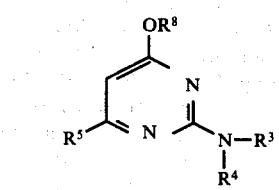

by conventional methods; in these formulae, $R^1$, $R^2$, $R^3$, $R^4$ and $R^5$ have the above meanings and $R^7$ and $R^8$ independently of one another are hydrogen, alkyl of 1 to 4 carbon atoms or C-acyl of a total of 2 to 7 carbon atoms.

The condensation is preferably carried out in the presence of acid dehydrating agents, eg., sulfuric acid, polyphosphoric acid, acetic anhydride or zinc chloride, at elevated temperatures, preferably at from 60° to 160° C. It is advantageous to carry out the condensation in the presence of solvents, preferably of acid solvents, eg. formic acid, acetic acid, propionic acid or mixtures of these. As a rule, the reaction has ended after from 2 to 8 hours. A suitable method of working up is to introduce the cooled reaction mixture into ice and water and separate off the product which has precipitated. The crude product can be purified by reprecipitation or recrystallization.

Specific examples of suitable benzoylbenzoic acids of the formula II are 2-(4'-dimethylamino-2'-hydroxybenzoyl)-benzoic acid, 2-(4'-diethylamino-2'-hydroxybenzoyl)-benzoic acid, 2-(4'dipropylamino-2'-hydroxybenzoyl)-benzoic acid, 2-(4'-dibutylamino-2'-hydroxybenzoyl)-benzoic acid, 2-(4'-o-toluidino-2'-hydroxybenzoyl)-benzoic acid, 2-(4'-o-chlorophenylamino-2'-hydroxybenzoyl)-benzoic acid, 2-(4'-p-toluidino-2'-hydroxybenzoyl)-benzoic acid and 2-(4'-p-chlorophenylamino -2'-hydroxybenzoyl)-benzoic acid.

The pyrimidines of the formula III are manufactured by the process disclosed in German Published Application No. 1,670,109, by addition reaction of an amine of the formula

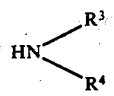
(IV)

with cyanamide, and reaction of the resulting guanidine of the formula

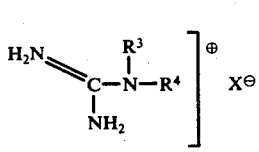
(V)

with benzoylacetic acid esters of the formula

(VI)

In this formula, $R^9$ is alkyl of 1 to 4 carbon atoms.

Examples of suitable pyrimidines of the formula III are 2-dibutylamino-6-phenyl-4-hydroxy-pyrimidine, 2-diethylamino-6-phenyl- 4-hydroxy-pyrimidine, 2-dimethylamino-6-phenyl-4-hydroxy-pyrimidine, 2-(N-methyl-N-cyclohexylamino)-6-phenyl-4-hydroxy-pyrimidine, 2-(1',1'-dimethylpropylamino)-6-phenyl-4-hydroxy-pyrimidine, 2-pyrrolidino-4-hydroxy-6-phenyl-pyrimidine, 2-piperidino-4-hydroxy-6-phenyl-pyrimidine, 2-morpholino-6-phenyl-4-hydroxy-pyrimidine, 2-(4'-methylpiperazino)j-6-phenyl-4-hydroxy-pyrimidine, 2-(N-methyl-N-benzylamino)-4-hydroxy-6-phenylpyrimidine, 2-N,N-di-β-methoxyethylamino-6-phenyl-4-hydroxy-pyrimidine, 2N,N-di-β-ethoxyethylamino-6-phenyl -4-hydroxy-pyrimidine, 2-N,N-dicyclohexylamino-6-phenyl-4-hydroxypyrimidine, 1-(2',6'-dimethylmorpholino)-6-phenyl-4-hydroxypyrimidine, 2-dibutylamino-6-(4'-methoxyphenyl)-4-hydroxypyrimidine, 2-dibutylamino-6-(4'-chlorophenyl)-4-hydroxypyrimidine, 2-dibutylamino-6-(4'-tolyl)-4-hydroxy-pyrimidine and 2-hexamethyleneimino-6-phenyl-4-hydroxy-pyrimidine. The above hydroxypyrimidines ($R^8=$ H) may also be present in the tautomeric pyrimidone form.

The lactones obtained, of the formula I, are colorless compounds. When treated, as such or as a solution in, eg., hydrocarbons, aliphatic or aromatic chlorohydrocarbons, ketones, ethers, esters and alcohols, with acid substances, the lactone ring is split and deeply colored dye salts are obtained. Since this reaction is even brought about by substances such as kaolin, zeolites, bentonites, silica and acid condensation products, eg., condensation products of phenolsulfonic acids and formaldehyde, which may be used for coating paper, or incorporation into paper, the above lactones are outstandingly suitable for use as dye intermediates for pressure-sensitive recording materials and in particular for the manufacture of copying papers. For example, they may be converted to a paste which is coated onto paper, after which the surface is provided with a protective layer. A particularly advantageous process is to microencapsulate a solution of the dye intermediate in a nonvolatile or only slightly volatile solvent, eg., dodecylbenzene, chloroparaffins, trichlorophenyl, monoalkyl-substituted or polyalkyl-substituted benzene, naphthalene or indan, mineral oils, spindle oil or phenylindans, and to coat the paper with these capsules. In contact with an acid receptive coating, the image of the writing is formed under writing pressure. The hue produced is predominantly in the red region of the spectrum, and possesses high intensity and luminosity. Compared to the intermediates of red dyes, disclosed in German Published Application No. 2,243,483, the new lactones have the advantage that the lactone form is more stable. This means that the red hue only develops on the acid receptive coating and the lactone-coated paper remains virtually unstained. As a result, the ghost writing on the donor side, a highly undesirable feature of copying papers, is avoided. In spite of their improved stability, the lactones according to the invention react instantly with acid substances, eg. those present in receptive coatings, to form the colored salts. The full depth of color is developed virtually instantly.

The new lactones are very suitable for use with intermediates of blue and yellow dyes, so as to produce black mixtures. For this purpose, a mixture of individually encapsulated dye intermediates may be used, or a solution of a mixture of the dye intermediates in an organic solvent may be encapsulated.

In the Examples which follow, parts and percentages are by weight.

EXAMPLE 1

A mixture of 41.6 parts of N,N-dibutylguanidine hydrochloride, 36 parts of sodium methylate (as a 30 per cent strength solution in methanol) and 38.4 parts of benzoylacetic acid ethyl ester is heated to the boil for 8 hours. After the solution has cooled, 500 parts by volume of water and 100 parts by volume of 30 per cent strength acetic acid are added and the precipitate formed is filtered off, washed with water and methanol and dried in vacuo at 60° C. The yield of 2-dibutylamino-6-phenyl-4-hydroxy-pyrimidine is 27 parts (melting point 128° C).

EXAMPLE 2

A mixture of 313 parts of 2-(4'-diethylamino-2'-hydroxybenzoyl)-benzoic acid, 299 parts of 2-dibutylamino-4-hydroxy-6-phenylpyrimidine, 1,000 parts of glacial acetic acid, 350 parts of acetic anhydride and 55 parts of concentrated sulfuric acid is heated for 4 hours at from 110° to 120° C. After the reaction solution has cooled, it is poured into 10,000 parts of ice and water, whilst stirring vigorously. After adding 50 parts of 50 per cent strength sodium hydroxide solution, the aqueous mixture is stirred for a further 4 hours and the product which was precipitated is then filtered off and washed with 5,000 parts of water. The moist crude product is extracted by boiling with methanol, the suspension is filtered and the residue is washed with methanol. After drying at 60° C, 431 parts of the compound of the formula

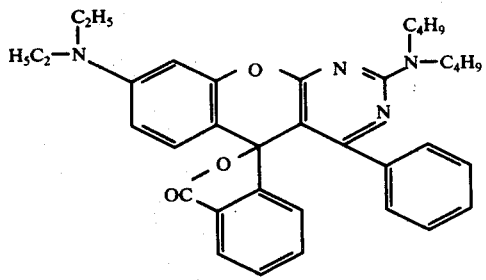

are obtained. Melting point 101°–103° C.

A solution of this compound in dodecylbenzene is microencapsulated and applied, in this form, to the surface of papers. On writing on the uncoated side of the paper, the capsules on the rear face are destroyed and as a result the contents of the capsules come into contact with the acid receptive coating of the sheet of paper underneath the rear face, forming a bluish red image.

EXAMPLE 3

196 parts of concentrated sulfuric acid are added to a solution of 370 parts of piperidine in 900 parts by volume of isobutanol, whilst cooling. The mixture is then heated to the boil. 420 parts of a 50 per cent strength aqueous solution of cyanamide are added dropwise in the course of 4 hours. The mixture is heated at the boil for 2 hours and the solvent is then distilled off. 720 parts of sodium methylate (as a 30 per cent strength solution in methanol) and 768 parts of benzoylacetic acid ethyl ester are added to the residue and this mixture is heated at the boil for 6 hours. 850 parts by volume of a mixture of methanol and ethanol are then distilled off and the 2-piperidino-6-phenyl-4-hydroxy-pyrimidine is precipitated by adding 1,500 parts by volume of water and 150 parts of glacial acetic acid. The product is filtered off, washed with water and acetone and dried in vacuo at 60° C. The yield is 590 parts (melting point: 207°–209° C).

EXAMPLE 4

A mixture of 313 parts of 2-(4'-diethylamino-2'-hydroxybenzoyl)-benzoic acid, 255 parts of 2-piperidino-4-hydroxy-6-phenylpyrimidine, 1,000 parts of glacial acetic acid, 350 parts of acetic anhydride and 55 parts of concentrated sulfuric acid is heated at 100°–110° C for 8 hours. When the reaction solution has cooled, it is poured into 10,000 parts of ice and water, the batch is stirred for a further 3 hours and the compound which has precipitated is filtered off and washed with 5,000 parts of water. The moist crude product is extracted by boiling with methanol, the suspension is filtered and the residue is washed and dried. A yield of 428 parts of the compound of the formula

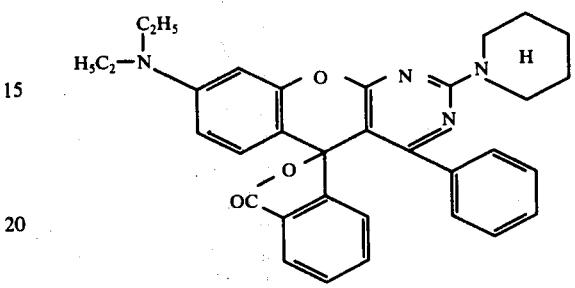

is obtained. Melting point 240°–241° C.

EXAMPLES 5 to 24

Analogously to Examples 2 to 4, the benzoylbenzoic acids of the formula

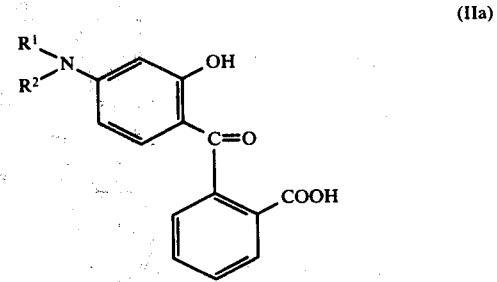

(IIa)

and the pyrimidines of the formula

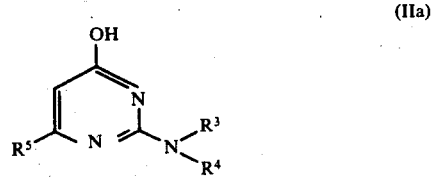

(IIa)

give the dye intermediates shown in the Examples which follows:

| Ex. | IIa $R^1$ $R^2$ | $R^5$ | IIIa $R^3$ $R^4$ | Dye intermediate | Hue |
|---|---|---|---|---|---|
| 5 | -N(C₂H₅)(C₂H₅) | phenyl | -N(CH₃)(cyclohexyl-H) |  | bluish red |
| 6 | -N(C₂H₅)(C₂H₅) | phenyl | -N(CH₃)(CH₃) |  | " |
| 7 | " | phenyl | -NH-C(CH₃)(CH₃)(CH₂CH₃) | 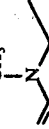 | red |

-continued
| Ex. | IIa $-N\begin{smallmatrix}R^1\\R^2\end{smallmatrix}$ | $R^5$ | IIIa $-N\begin{smallmatrix}R^3\\R^4\end{smallmatrix}$ | Dye intermediate | Hue |
|---|---|---|---|---|---|
| 8 | " |  |  |  | bluish red |
| 9 | " |  | $-N\begin{smallmatrix}C_2H_5\\C_2H_5\end{smallmatrix}$ |  | " |
| 10 | $-N\begin{smallmatrix}C_2H_5\\C_2H_5\end{smallmatrix}$ |  |  |  | " |

-continued

| Ex. | IIa $-N{<}^{R^1}_{R^2}$ | $R^5$ | IIIa $-N{<}^{R^3}_{R^4}$ | Dye intermediate | Hue |
|---|---|---|---|---|---|
| 11 | " | phenyl | morpholino | (rhodamine-type structure with morpholine group) | red |
| 12 | " | phenyl | $-N{<}^{CH_2C_6H_5}_{CH_3}$ | (rhodamine-type structure with N-benzyl-N-methyl group) | " |
| 13 | " | phenyl | $-N{<}^{C_2H_4-OCH_3}_{C_2H_4-OCH_3}$ | (rhodamine-type structure with bis(methoxyethyl)amino group) | " |

-continued

| Ex. | IIa $-N\begin{matrix}R^1\\R^2\end{matrix}$ | IIIa R$^5$ | IIIa $-N\begin{matrix}R^3\\R^4\end{matrix}$ | Dye intermediate | Hue |
|---|---|---|---|---|---|
| 14 | " | 4-OCH$_3$-C$_6$H$_4$- | $-N(C_4H_9)_2$ | (structure with 4-OCH$_3$ aryl, dibutylamino pyrimidine, diethylamino xanthene, 2-methoxyphenyl) | bluish red |
| 15 | $-N(C_2H_5)_2$ | 4-Cl-C$_6$H$_4$- | $-N(C_4H_9)_2$ | (structure with 4-Cl aryl) | " |
| 16 | " | 4-CH$_3$-C$_6$H$_4$- | $-N(C_4H_9)_2$ | (structure with 4-CH$_3$ aryl) | " |

-continued

| Ex. | IIa $-N{<}^{R^1}_{R^2}$ | $R^5$ | IIIa $-N{<}^{R^3}_{R^4}$ | Dye intermediate | Hue |
|---|---|---|---|---|---|
| 17 | $-N{<}^{CH_3}_{CH_3}$ | phenyl | $-N{<}^{C_4H_9}_{C_4H_9}$ | (structure) | bluish red |
| 18 | $-N{<}^{CH_3}_{CH_3}$ | phenyl | $-N{<}^{C_2H_4-OC_2H_5}_{C_2H_4-OC_2H_5}$ | (structure) | red |
| 19 | $-N{<}^{CH_3}_{CH_3}$ | phenyl | piperidino | (structure) | bluish red |

-continued
| Ex. | IIa $R^1$ $R^2$ | $R^5$ | IIIa $R^3$ $R^4$ | Dye intermediate | Hue |
|---|---|---|---|---|---|
| 20 |  |  |  | 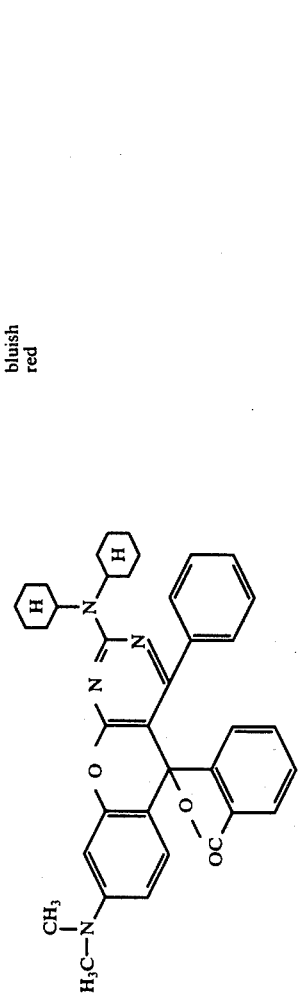 | bluish red |
| 21 |  |  |  |  | " |
| 22 | 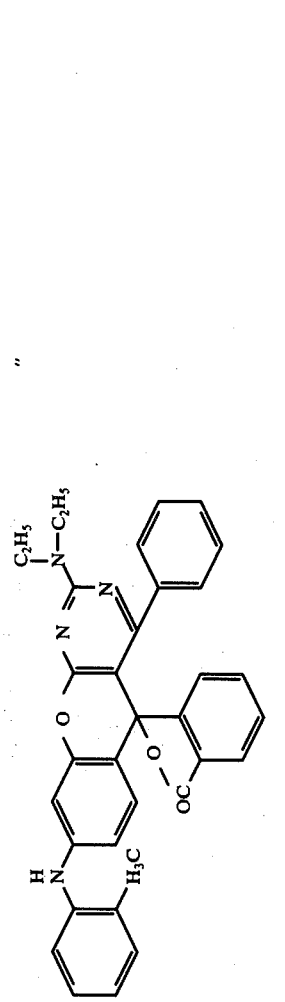 |  |  |  | " |

-continued

| Ex. | IIa $-N\begin{matrix}R^1\\R^2\end{matrix}$ | $R^5$ | IIIa $-N\begin{matrix}R^3\\R^4\end{matrix}$ | Dye intermediate | Hue |
|---|---|---|---|---|---|
| 23 | $-N\begin{matrix}C_2H_5\\C_2H_5\end{matrix}$ | tolyl | 2,6-dimethylmorpholino | (structure) | red |
| 24 | $-N\begin{matrix}C_2H_5\\C_2H_5\end{matrix}$ | tolyl | $-N(CH_2)_6$ | (structure) | bluish red |

We claim:
1. A diazarhodamine-lactone of the formula

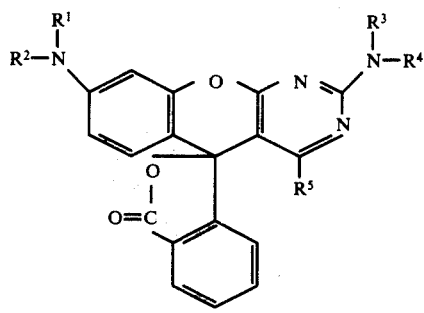

where $R^1$ is hydrogen or alkyl of 1 to 4 carbon atoms, $R^2$ is alkyl of 1 to 4 carbon atoms, unsubstituted phenyl, or phenyl in which 1 or 2 hydrogens are replaced by alkyl of 1 to 3 carbon atoms, chlorine or bromine, the substituents being identical or different, $R^3$ and $R^4$ independently of one another are hydrogen, alkyl of 1 to 7 carbon atoms, cycloalkyl of 5 to 7 carbon atoms, phenylalkyl of 7 to 10 carbon atoms or alkoxyalkyl of a total of 3 to 8 carbon atoms, or the group

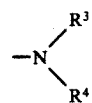

is a pyrrolidine, piperidine, piperazine, N-methylpiperazine, N-ethylpiperazine or hexamethyleneimine radical, and $R^5$ is unsubstituted phenyl or phenyl which is substituted by alkyl of 1 to 3 carbon atoms, methoxy, ethoxy, chlorine.

2. A diazarhodamine-lactone as claimed in claim 1, wherein $R^1$ is hydrogen, methyl or ethyl, $R^2$ is methyl, ethyl, o-tolyl, p-tolyl, o-chlorophenyl or p-chlorophenyl, $R^3$ and $R^4$ independently of one another are methyl, ethyl, propyl, butyl, cyclohexyl, benzyl, β-methoxyethyl or β-ethoxyethyl or the group

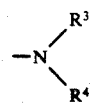

is a N-pyrrolidine, piperidine or N-(N'-methylpiperazine) radical and $R^5$ is phenyl or methoxyphenyl.

3. A diazarhodamine-lactone as claimed in claim 1, wherein $R^1 = R^2$ and both are methyl or ethyl, $R^3$ and $R^4$ independently of one another are methyl, ethyl, propyl, butyl, cyclohexyl, benzyl, β-methoxyethyl or β-ethoxyethyl or the group

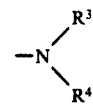

is a pyrrolidine, N-piperidine or N-(N'-methylpiperazine) radical and $R^5$ is phenyl.

4. A diazarhodamine-lactone of the formula

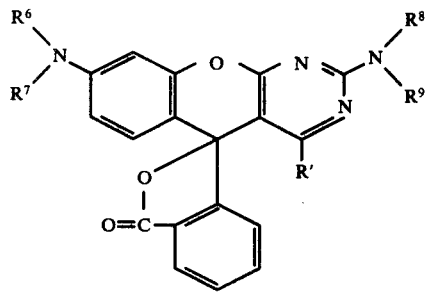

where $R^6$ and $R^7$ are methyl or ethyl, $R^8$ and $R^9$ are butyl and R' is phenyl or methoxyphenyl.

5. The diazarhodamine-lactone of the formula

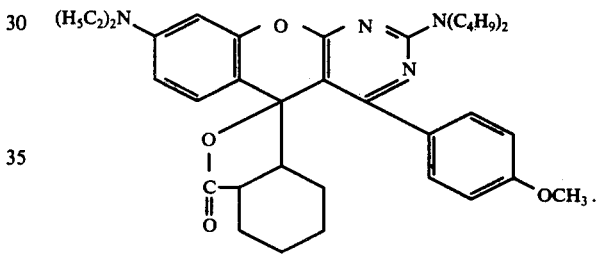

6. The diazarhodamine-lactone of the formula

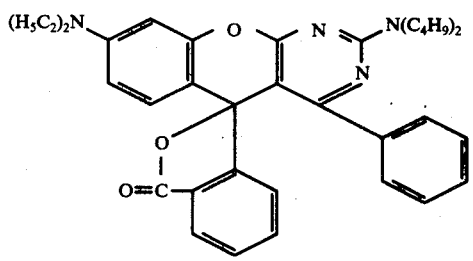

* * * * *

UNITED STATES PATENT AND TRADEMARK OFFICE
CERTIFICATE OF CORRECTION

PATENT NO. : 4,052,398
DATED : October 4, 1977
INVENTOR(S) : Hellmut Kast et al

It is certified that error appears in the above-identified patent and that said Letters Patent are hereby corrected as shown below:

Page 1, in the Abstract, 6 lines from the end, after "methoxy," insert --ethoxy,--.

Signed and Sealed this

Eighth Day of August 1978

[SEAL]

Attest:

RUTH C. MASON
Attesting Officer

DONALD W. BANNER
Commissioner of Patents and Trademarks